(12) United States Patent
Maa

(10) Patent No.: US 6,737,101 B2
(45) Date of Patent: May 18, 2004

(54) PARTICLE FORMATION

(75) Inventor: Yuh-Fun Maa, Millbrae, CA (US)

(73) Assignee: Powderject Research Limited, Oxford (GB)

( * ) Notice: Subject to any disclaimer, the term of this patent is extended or adjusted under 35 U.S.C. 154(b) by 0 days.

(21) Appl. No.: 10/397,329

(22) Filed: Mar. 27, 2003

(65) Prior Publication Data

US 2003/0190366 A1 Oct. 9, 2003

Related U.S. Application Data

(62) Division of application No. 09/410,692, filed on Oct. 1, 1999, now Pat. No. 6,613,360.
(60) Provisional application No. 60/102,726, filed on Oct. 1, 1998.

(51) Int. Cl.[7] .............................. B01J 13/00; A61K 9/16
(52) U.S. Cl. ....................................... 427/2.14; 424/490
(58) Field of Search ................... 424/489–498; 514/951; 428/402, 402.24, 403–407; 427/2.14, 2.15, 2.16, 2.18, 2.19, 2.21, 2.22

(56) References Cited

U.S. PATENT DOCUMENTS

| 5,630,796 A | 5/1997 | Bellhouse et al. |
| 5,985,309 A | 11/1999 | Edwards et al. |
| 5,997,905 A | 12/1999 | McTeigue et al. |
| 6,001,395 A | 12/1999 | Coombes et al. |
| 6,068,858 A | 5/2000 | Liversidge et al. |

FOREIGN PATENT DOCUMENTS

| EP | 0532777 A1 | 3/1993 |
| WO | WO 93/00991 | 1/1993 |
| WO | WO 94/23738 | 10/1994 |
| WO | WO 94/24363 | 10/1994 |
| WO | WO 96/04947 | 2/1996 |
| WO | WO 96/12513 | 5/1996 |
| WO | WO 96/20022 | 7/1996 |
| WO | WO 97/48485 | 12/1997 |
| WO | WO 98/10750 | 3/1998 |

OTHER PUBLICATIONS

Iyer et al. (1993) *Drug Devel. Ind. Pharm.* 19:981–998.
Maa et al. (1996) *Intl. J. Pharmaceutics* 144:47–59.
Olsen et al. (Jan. 1989) *Pharm. Technol.* 13:34–46.
Olsen et al. (Jun. 1989) *Pharm. Technol.* 13:39–50.

*Primary Examiner*—Sharon Kennedy
(74) *Attorney, Agent, or Firm*—Foley & Lardner

(57) ABSTRACT

Spray-coated pharmaceutical powder compositions for transdermal administration using a needleless syringe comprise seed particles coated with a pharmaceutical composition, the said coated seed particles having an average size of about 10 to 100 $\mu$m and having an envelope density ranging from about 0.1 to about 25 g/cm$^3$.

34 Claims, No Drawings

PARTICLE FORMATION

CROSS-REFERENCE TO RELATED APPLICATIONS

This application is a divisional of U.S. patent application Ser. No. 09/410,692, filed Oct. 1, 1999, now U.S. Pat No. 6,613,360, issued Sep. 2, 2003 and is related to U.S. provisional application serial No. 60/102,726, filed Oct. 1, 1998, from which applications priority is claimed pursuant to 35 U.S.C. §§119(e)(1) and 120 and which applications are incorporated herein by reference in their entirety.

TECHNICAL FIELD

The invention relates to a method for producing powdered pharmaceutical compositions. More specifically, the invention relates to a method for forming dense, substantially solid particles from pharmaceutical compositions, where the particulate compositions are particularly suitable for transdermal particle delivery from a needleless syringe system.

BACKGROUND

The ability to deliver pharmaceuticals through skin surfaces (transdermal delivery) provides many advantages over oral or parenteral delivery techniques. In particular, transdermal delivery provides a safe, convenient and noninvasive alternative to traditional drug administration systems, conveniently avoiding the major problems associated with oral delivery (e.g., variable rates of absorption and metabolism, gastrointestinal irritation and/or bitter or unpleasant drug tastes) or parenteral delivery (e.g., needle pain, the risk of introducing infection to treated individuals, the risk of contamination or infection of health care workers caused by accidental needle-sticks and the disposal of used needles).

However, despite its clear advantages, transdermal delivery presents a number of its own inherent logistical problems. The passive delivery of drugs through intact skin necessarily entails the transport of molecules through a number of structurally different tissues, including the stratum corneum, the viable epidermis, the papillary dermis, and the capillary walls in order for the drug to gain entry into the blood or lymph system. Transdermal delivery systems must therefore be able to overcome the various resistances presented by each type of tissue. In light of the above, a number of alternatives to passive transdermal delivery have been developed. These alternatives include the use of skin penetration enhancing agents, or "permeation enhancers," to increase skin permeability, as well as non-chemical modes such as the use of iontophoresis, electroporation or ultrasound. However, these alternative techniques often give rise to their own unique side effects, such as skin irritation or sensitization. Thus, the spectrum of pharmaceuticals that can be safely and effectively administered using traditional transdermal delivery methods has remained limited.

More recently, a novel transdermal drug delivery system that entails the use of a needleless syringe to fire powders (i.e., solid drug-containing particles) in controlled doses into and through intact skin has been described. In particular, commonly owned U.S. Pat. No. 5,630,796 to Bellhouse et al. describes a needleless syringe that delivers pharmaceutical particles entrained in a supersonic gas flow. The needleless syringe is used for transdermal delivery of powdered drug compounds and compositions, for delivery of genetic material into living cells (e.g., gene therapy) and for the delivery of biopharmaceuticals to skin, muscle, blood or lymph. The needleless syringe can also be used in conjunction with surgery to deliver drugs and biologics to organ surfaces, solid tumors and/or to surgical cavities (e.g., tumor beds or cavities after tumor resection). In theory, practically any pharmaceutical agent that can be prepared in a substantially solid, particulate form can be safely and easily delivered using such devices.

One particular needleless syringe generally comprises an elongate tubular nozzle having a rupturable membrane initially closing the passage through the nozzle and arranged substantially adjacent to the upstream end of the nozzle. Particles of a therapeutic agent to be delivered are disposed adjacent to the rupturable membrane and are delivered using an energizing means which applies a gaseous pressure to the upstream side of the membrane sufficient to burst the membrane and produce a supersonic gas flow (containing the pharmaceutical particles) through the nozzle for delivery from the downstream end thereof. The particles can thus be delivered from the needleless syringe at delivery velocities of between Mach 1 and Mach 8 which are readily obtainable upon the bursting of the rupturable membrane.

Another needleless syringe configuration generally includes the same elements as described above, except that instead of having the pharmaceutical particles entrained within a supersonic gas flow, the downstream end of the nozzle is provided with a bistable diaphragm which is moveable between a resting "inverted" position (in which the diaphragm presents a concavity on the downstream face to contain the pharmaceutical particles) and an active "everted" position (in which the diaphragm is outwardly convex on the downstream face as a result of a supersonic shockwave having been applied to the upstream face of the diaphragm). In this manner, the pharmaceutical particles contained within the concavity of the diaphragm are expelled at a supersonic initial velocity from the device for transdermal delivery thereof to a targeted skin or mucosal surface.

Transdermal delivery using either of the above-described needleless syringe configurations is carried out with particles having an approximate size that generally ranges between 0.1 and 250 $\mu$m. For drug delivery, an optimal particle size is usually at least about 10 to 15 $\mu$m (the size of a typical cell). For gene delivery, an optimal particle size is generally substantially smaller than 10 $\mu$m. Particles larger than about 250 $\mu$m can also be delivered from the device, with the upper limitation being the point at which the size of the particles would cause untoward damage to the skin cells. The actual distance which the delivered particles will penetrate depends upon particle size (e.g., the nominal particle diameter assuming a roughly spherical particle geometry), particle density, the initial velocity at which the particle impacts the skin surface, and the density and kinematic viscosity of the skin. In this regard, optimal particle densities for use in needleless injection generally range between about 0.1 and 25 $g/cm^3$, preferably between about 0.8 and 1.5 $g/cm^3$, and injection velocities generally range between about 100 and 3,000 m/sec.

SUMMARY OF THE INVENTION

It is a primary object of the invention to provide a spray-coated powder composition for administration from a needleless syringe. It is also a primary object of the invention to provide suitable spray-coating methods for producing such powder compositions.

In one aspect of the invention, a spray-coated powder composition for administration from a needleless syringe is provided. The powder composition is formed from seed particles that are coated with an aqueous pharmaceutical composition. More especially, the spray-coated powder composition comprises seed particles coated with a pharmaceutical composition, the said coated seed particles having an average size of about 10 to 100 μm and having an envelope density ranging from about 0.1 to about 25 g/cm$^3$.

The coated seed particles can have an average size of about 20 to 70 μm. Preferably, they have an envelope density ranging from about 0.8 to about 1.5 $g/cm^3$. The coated seed particles typically have a substantially spherical aerodynamic shape and/or a substantially uniform, nonporous surface. The powders may also be characterized in that the coated seed particles have a pharmaceutical composition loading of about 1 to 50 wt %. The spray-coated powder compositions can contain, as the active pharmaceutical agent, any small molecule drug substance, organic or inorganic chemical, vaccine, or peptide (polypeptide and/or protein) of interest.

In another aspect of the invention, a method for preparing the spray-coated powder composition is provided. The method comprises spray-coating an aqueous pharmaceutical composition onto seed particles under conditions sufficient to provide coated particles having an average size of about 10 to 100 μm and an envelope density ranging from about 0.1 to about 25 $g/cm^3$. In one particular embodiment, the method entails the steps of: (a) suspending the seed particles in a reaction chamber using a hot air flow; (b) atomizing an aqueous pharmaceutical composition into a fine spray and introducing the spray into the reaction chamber; (c) allowing the spray to spread over the surface of the suspended seed particles to coat them with a thin film; and then (d) drying the coated seed particles. If desired, the aqueous pharmaceutical composition can be sprayed into the reaction chamber in a direction that is transverse to the direction of the hot air flow.

It is an advantage of the invention that free-flowing powder compositions can be produced having well defined particle size, density and mechanical properties which collectively are suitable for transdermal delivery from a needleless syringe. Further advantages of the methods of the invention include flexible pharmaceutical loading (up to about 50 wt %), overall process efficiency (no need for post-formulation fractionation, classification or sieving operations), and the methods are readily scalable. The invention further provides:

- a dosage receptacle for a needleless syringe, said receptacle containing a therapeutically effective amount of a spray-coated powder composition of the invention; and
- a needleless syringe which is loaded with such a powder composition.

These and other objects, aspects, embodiments and advantages of the present invention will readily occur to those of ordinary skill in the art in view of the disclosure herein.

DETAILED DESCRIPTION OF THE PREFERRED EMBODIMENTS

Before describing the present invention in detail, it is to be understood that this invention is not limited to particularly exemplified compositions or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a particle" includes a mixture of two or more such particles, reference to "an excipient" includes mixtures of two or more such excipients, and the like.

A. Definitions

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

By "transdermal delivery," applicant intends to include both transdermal ("percutaneous") and transmucosal routes of administration, i.e., delivery by passage of a drug or pharmaceutical agent through the skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdermal Delivery of Drugs*, Vols. 1–3, Kydonieus and Berner (eds.), CRC Press, (1987).

As used herein, the term "pharmaceutical" or "pharmaceutical agent" intends any compound or composition of matter which, when administered to an organism (human or animal) induces a desired pharmacologic and/or physiologic effect by local and/or systemic action. The term therefore encompasses those compounds or chemicals traditionally regarded as drugs, as well as biopharmaceuticals including molecules such as peptides, hormones, nucleic acids, gene constructs and the like. More particularly, the term "pharmaceutical" or "pharmaceutical agent" includes compounds or compositions for use in all of the major therapeutic areas including, but not limited to, anti-infectives such as antibiotics and antiviral agents; analgesics and analgesic combinations; local and general anesthetics; anorexics; antiarthritics; antiasthmatic agents; anticonvulsants; antidepressants; antihistamines; anti-inflammatory agents; antinauseants; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; therapeutic proteins (e.g., antigens, antibodies, growth factors, cytokines, interleukins, lymphokines, interferons, enzymes, etc.), peptides and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like).

The above pharmaceuticals or pharmaceutical agents, alone or in combination with other agents, are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include water, silicone, gelatin, waxes, and like materials. Examples of normally employed "excipients," include pharmaceutical grades of carbohydrates including monosaccharides, disaccharides, cyclodextrans, and polysaccharides (e.g., dextrose, sucrose, lactose, trehalose, raffinose, mannitol, sorbitol, inositol, dextrans, and maltodextrans); starch; cellulose; salts (e.g. sodium or calcium phosphates, calcium sulfate, magnesium sulfate); citric acid; tartaric acid; glycine; high molecular weight polyethylene glycols (PEG); Pluronics; surfactants; and combinations thereof. Generally, when carriers and/or excipients are used, they are used in amounts ranging from about 0.1 to 99 wt % of the pharmaceutical composition.

The terms "individual" and "subject" are used interchangeably herein to refer to any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms do not denote a particular age. Thus, both adult and newborn individuals are intended to be covered. The methods described herein are intended for use in any of the above vertebrate species, since the immune systems of all of these vertebrates operate similarly.

The term "powder," as used herein, refers to a composition that consists of substantially solid particles that can be delivered transdermally using a needleless syringe device. The particles that make up the powder can be characterized on the basis of a number of parameters including, but not limited to, the average particle size, the average particle density, particle morphology (e.g., particle aerodynamic shape and particle surface characteristics), and particle penetration energy (P.E.).

The average particle size of the powders produced according to the present invention can vary widely and is generally between about 10 and 100 µm, more typically between about 20 and 70 µm. The average particle size of the powder can be measured as a mass mean aerodynamic diameter (MMAD) using conventional techniques such as microscopic techniques (where particles are sized directly and individually rather than grouped statistically), absorption of gasses, permeability or time of flight. If desired, automatic particle-size counters can be used (e.g., Aerosizer Counter, Coulter Counter, HIAC Counter, or Gelman Automatic Particle Counter) to ascertain the average particle size.

Actual particle density, or "absolute density," can be readily ascertained using known quantification techniques such as helium pycnometry and the like. Alternatively, envelope ("tap") density measurements can be used to assess the density of a particulate pharmaceutical composition produced according to the methods of the invention. Envelope density information is particularly useful in characterizing the density of objects of irregular size and shape. Envelope density is the mass of an object divided by its volume, where the volume includes that of its pores and small cavities but excludes interstitial space. A number of methods of determining envelope density are known in the art, including wax immersion, mercury displacement, water absorption and apparent specific gravity techniques. A number of suitable devices are also available for determining envelope density, for example, the Geopyc™ Model 1360, available from the Micromeritics Instrument Corp. The difference between the absolute density and envelope density of a sample pharmaceutical composition provides information about the sample's percentage total porosity and specific pore volume.

Particle morphology, particularly the aerodynamic shape of a particle, can be readily assessed using standard light microscopy. It is preferred that the particles which make up the instant powders have a substantially spherical or at least substantially elliptical aerodynamic shape. It is also preferred that the particles have an axis ratio of 3 or less to avoid the presence of rod- or needle-shaped particles. These same microscopic techniques can also be used to assess the particle surface characteristics, e.g., the amount and extent of surface voids or degree of porosity.

Particle penetration energies can be ascertained using a number of conventional techniques, for example a metallized film P.E. test.

B. General Methods

In one embodiment, a powdered pharmaceutical composition is provided, wherein the powder composition (which is comprised of particles) is produced using a spray-coating technique. The powders are suitable for transdermal administration from a needleless syringe delivery system, and as such, the particles which make up the powdered composition must have sufficient physical strength to withstand sudden acceleration to several times the speed of sound and the impact with, and passage through, the skin and tissue. The particles are formed by spray-coating an aqueous pharmaceutical composition onto suitable seed particles. The particles can be delivered from a needleless syringe system such as those described in commonly owned International Publication Nos. WO 94/24263, WO 96/04947, WO 96/12513, and WO 96/20022, all of which are incorporated herein by reference.

The aqueous pharmaceutical compositions can contain, as the active pharmaceutical agent, any small molecule drug substance, organic or inorganic chemical, vaccine, or peptide (polypeptide and/or protein) of interest. In particular embodiments, the pharmaceutical agent is a biopharmaceutical preparation of a peptide, polypeptide, protein or any other such biological molecule. Exemplary peptide and protein formulations include, without limitation, insulin; calcitonin; octreotide; endorphin; liprecin; pituitary hormones (e.g., human growth hormone and recombinant human growth hormone (hGH and rhGH), HMG, desmopressin acetate, etc); follicle luteoids; growth factors (such as growth factor releasing factor (GFRF), somatostatin, somatotropin and platelet-derived growth factor); asparaginase; chorionic gonadotropin; corticotropin (ACTH); erythropoietin (EPO); epoprostenol (platelet aggregation inhibitor); glucagon; interferons; interleukins; menotropins (urofollitropin, which contains follicle-stimulating hormone (FSH); and luteinizing hormone (LH)); oxytocin; streptokinase; tissue plasminogen activator (TPA); urokinase; vasopressin; desmopressin; ACTH analogues; angiotensin II antagonists; antidiuretic hormone agonists; bradykinin antagonists; CD4 molecules; antibody molecules and antibody fragments (e.g., Fab, $Fab_2$, Fv and sFv molecules); IGF-1; neurotrophic factors; colony stimulating factors; parathyroid hormone and agonists; parathyroid hormone antagonists; prostaglandin antagonists; protein C; protein S; renin inhibitors; thrombolytics; tumor necrosis factor (TNF); vaccines (particularly peptide vaccines including subunit and synthetic peptide preparations); vasopressin antagonists analogues; and α-1 antitrypsin. Additionally, nucleic acid preparation, such as vectors or gene constructs for use in subsequent gene delivery, can be used.

The pharmaceutical agent is typically prepared as an aqueous pharmaceutical composition using a suitable aqueous carrier, along with suitable excipients, protectants, solvents, salts, surfactants, buffering agents and the like. Suitable excipients can include free-flowing particulate solids that do not thicken or polymerize upon contact with water, which are innocuous when administered to an individual, and do not significantly interact with the pharmaceutical agent in a manner that alters its pharmaceutical activity. In general, excipients which are sticky, or have high hygroscopicity are avoided particularly for powder formulations where the pharmaceutical is loaded onto the seed particle at a high concentration (e.g., >10 wt %). Examples of normally employed excipients include, but are not limited to, pharmaceutical grades of dextrose, sucrose, lactose, trehalose, mannitol, sorbitol, inositol, dextran, starch, cellulose, sodium or calcium phosphates, calcium carbonate, calcium sulfate, sodium citrate, citric acid, tartaric acid, glycine, high molecular weight polyethylene glycols (PEG), and combinations thereof. Suitable solvents include, but are not limited to, methylene chloride, acetone, methanol, ethanol, isopropanol and water. Generally pharmaceutically acceptable salts having molarities ranging from about 1 mM to 2M can be used. Pharmaceutically acceptable salts include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in REMINGTON'S PHARMACEUTICAL SCIENCES (Mack Pub. Co., N.J. 1991), incorporated herein by reference.

The seed particles can be comprised of any parenterally acceptable powder (e.g., crystalline or amorphous), are selected to have good flowability (i.e., are fluidizable), and are sufficiently dense for efficient use with needleless transdermal delivery systems. Crystalline particles are generally preferred due to their inherently high particle density and overall penetration energy. Seed particles having an overall spherical or at least elliptical shape are preferred. Particles generally are selected to have an axis ratio of 3 or less, for example 2 or less or 1.5 or less, in order to avoid rod- or needle-shaped particles which are difficult to reprocess and are generally less flowable.

Suitable seed particles can be comprised of any pharmaceutically acceptable carbohydrate (e.g., sugars such as lactose, mannitol, trehalose, etc.), polysaccharide, starch, biodegradable polymer (e.g. PLGA, a copolymer of L-lactic acid and glycolic acid), or the like. The seed particles can have an average size of about 5 to 100 $\mu$m, for example about 10 to 95 $\mu$m or about 20 to 70 $\mu$m. Seed particle preparations having a substantially homogenous average particle size can be readily obtaining using standard sieving or other particle classification methodologies.

The spray-coated powders can be formed using any standard spray-coating processing apparatus. In this regard, batch-type fluid-bed processors have long been used to perform drying, granulation, and coating operations in the pharmaceutical industry for preparing solid dosage forms. Olsen, K. W. (1989) "Batch fluid-bed processing equipment: A design overview," Part I., *Pharm. Technol.* 13:34–46, Olsen, K. W. (1989) "Batch fluid-bed processing equipment: A design overview," Part II., *Pharm. Technol.* 13:39–50. With the advent of the Würster spray coater, seed particles as small as 50 $\mu$m in size can, at least in theory, be coated. Iyer et al. (1993) *Drug Devel. Ind. Pharm.* 19:981–989. However, to date, the spray coating of seed particles having an average size of 100 $\mu$m or less has been limited, particularly for protein or peptide pharmaceuticals. Maa et al. (1996) *Intl. J. Pharmaceutics* 144:47–59.

Spray coating processors that can fluidize seed particles of 10 $\mu$m or larger, for example 20 $\mu$m and larger, and which can atomize a fine spray (droplet size of 30 $\mu$m or less, preferably 10 $\mu$m or less) are preferred. Suitable processors include any commercially available Würster spray coater, or Würster HS spray coater (available from Glatt Air Techniques, Inc.). For fluid-bed processing, the spray coating processor can utilize any suitable spraying method which is selected in consideration of the desired characteristics for the finished product. These spraying methods (e.g., top, bottom or tangential (rotary coater)) are generally known to those skilled in the art.

The liquid delivery system for the spray coat processor typically utilizes a binary nozzle, where the aqueous pharmaceutical composition is supplied at a relatively low pressure through an orifice and is atomized by air. Pneumatic nozzles can be used to produce smaller droplets. The atomization conditions, including atomization gas flow rate, atomization gas pressure, liquid flow rate, etc., can be controlled to produce droplets from the pharmaceutical composition having an average diameter of about 30 $\mu$m or less, with droplets having an average size of 10 $\mu$m or less being preferred. Typically, the atomizing air pressure, liquid flow rate and the fluidizing air temperature and volume are the most significant process variables and have the greatest effect over the particle characteristics of the resultant coated particles. Drying temperature conditions of about 50–150° C. inlet temperature and about 30–100° C. outlet temperature are preferred. The thickness of the pharmaceutical coat can be controlled by the drying time, and the present methods can provide spray-coated powders formed from seed particles loaded with from about 1 to 50 wt % (e.g., about 0.5 to 15 wt % of active pharmaceutical agent in compositions containing both active pharmaceutical agent and carrier), preferably >10 wt % of the aqueous pharmaceutical composition.

If desired, a secondary coating process can be used to provide further structural integrity in the coated particles, for example, where the spray-coated powder particles are coated with a standard sugar excipient using the same sort of spray-coating procedure as described herein above. In some cases, it may be desirable to coat the spray-coated powder particles with the same sugar used as the seed (e.g., mannitol, lactose, trehalose, or the like). Other secondary coating materials include, but are not limited to, pharmaceutical grades of carbohydrates including monosaccharides, disaccharides, cyclodextrans, and polysaccharides (e.g., dextrose, sucrose, raffinose, mannose, sorbitol, inositol, dextrans, and maltodextrans); starch; cellulose; salts (e.g. sodium or calcium phosphates, calcium sulfate, magnesium sulfate); citric acid; tartaric acid; glycine; high molecular weight polyethylene glycols (PEG); Pluronics; surfactants; and combinations thereof. The secondary coating material can also be used to optimize the particles for delivery to mucosal target surfaces (e.g., by coating the spray-coated powder particles with a lipid), or to alter or retard solubility characteristics of the particles after delivery into an aqueous environment (e.g., by applying a secondary coating containing a salt, starch, dextran, or the like).

The spray-coating methods of the present invention can be used to produce powders that are suitable for transdermal delivery from a needleless syringe delivery device. Typical powders are characterized in that the individual particles have an average size in the range of about 20 to 70 µm, an envelope density ranging from about 0.1 to about 25 g/cm$^3$, preferably ranging from about 0.8 to about 1.5 g/cm$^3$, and have a substantially spherical aerodynamic shape with a substantially uniform, nonporous surface.

The particles which make up the spray-coated powders of the present invention will also have a particle penetration energy suitable for transdermal delivery from a needleless syringe device. Such penetration energies can conveniently be assessed using a metallized film P.E. measuring procedure as follows. A metallized film material (e.g., a 125 µm polyester film having a 350 Å layer of aluminum deposited on a single side) is used as a substrate into which the powder is fired from a needleless syringe (e.g., the needleless syringe described in U.S. Pat. No. 5,630,796 to Bellhouse et al.) at an initial velocity of about 100 to 3000 m/sec. The metallized film is placed, with the metal coated side facing upwards, on a suitable surface. A needleless syringe loaded with a spray-coated powder produced according to the methods of the invention is placed with its spacer contacting the film, and then fired. Residual powder is removed from the metallized film surface using a suitable solvent. Penetration energy is then assessed using a BioRad Model GS-700 imaging densitometer to scan the metallized film, and a personal computer with a SCSI interface and loaded with MultiAnalyst software (BioRad) and Matlab software (Release 5.1, The MathWorks, Inc.) is used to assess the densitometer reading. A program is used to process the densitometer scans made using either the transmittance or reflectance method of the densitometer. The penetration energy of the spray-coated powders should be equivalent to, or better than that of reprocessed mannitol particles of the same size (mannitol particles that are freeze-dried, compressed, ground and sieved according to the methods of commonly owned International Publication No. WO 97/48485, incorporated herein by reference).

Once produced, the spray-coated powders of the present invention can be packaged in individual unit dosages. As used herein, a "unit dosage" intends a dosage receptacle containing a therapeutically effective amount of a spray-coated pharmaceutical produced according to the methods of the present invention. The dosage receptacle is generally one which fits within a needleless syringe device to allow for transdermal delivery from the device. Such receptacles can be capsules, foil pouches, sachets, cassettes, or the like.

C. Experimental

Below are examples of specific embodiments for carrying out the methods of the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

The following spray-coated powder formulations are made using the methods of the present invention.

Formulation 1:

Seed particles: 500 grams of lactose (Pharmatose, 100M & 200M, Crompton & Knowle), sieved to provide an average particle size of 20–75 µm by jet sieve.

Aqueous pharmaceutical composition: Lysozyme (50%) and trehalose (50%) at a total solid concentration of 20%.

Spray coater: GPCG-1 (Glatt Air), operated at the following coating conditions: air inlet temperature=85° C., air outlet temperature=42° C., liquid feed=15 mL/min, air velocity in the bed=3.5 m/sec., coating loading 10% of lysozyme, and a coating time=35 min.

Formulation 2:

Seed particles: 300 grams of lactose (Pharmatose, 100M & 200M, Crompton & Knowle), sieved to provide an average particle size of 20–75 µm by jet sieve.

Aqueous pharmaceutical composition: s-Calcitonin (20%), mannitol (30%), and trehalose (50%) at a total solid concentration of 10%.

Spray coater: Precision coater (MP-1, Niro), operated at the following coating conditions: air inlet temperature=68° C., air outlet temperature =34° C., liquid feed=12 mL/min, air velocity in the bed=3.5 m/sec., coating loading 5% of s-Calcitonin, and a coating time=63 min.

Formulation 3:

Seed particles: 300 grams of mannitol (Merck), sieved to provide an average particle size of 20–75 µm by jet sieve.

Aqueous pharmaceutical composition: recombinant human growth hormone (rhGH) (50%), mannitol (20%), glycine (10%), and trehalose (20%) at a total solid concentration of 10%.

Spray coater: Precision coater (MP-1, Niro), operated at the following coating conditions: air inlet temperature=75° C., air outlet temperature =40° C., liquid feed=13 mL/min, air velocity in the bed=3.5 m/sec., coating loading 5% of rhGH, and a coating time=24 min.

Formulation 4:

Seed particles: 500 grams of mannitol (Merck), sieved to provide an average particle size of 20–75 µm by jet sieve.

Aqueous pharmaceutical composition: Bovine serum albumin (BSA) (100%) at a total solid concentration of 10%.

Spray coater: GPCG-1 (Glatt Air), operated at the following coating conditions: air inlet temperature=85° C., air outlet temperature=42° C., liquid feed=15 m/min, air velocity in the bed=3.5 m/sec., coating loading 15% of BSA, and a coating time=50 min.

Formulation 5:

Seed particles: 300 grams of lactose (Pharmatose, 100M & 200M, Crompton & Knowle), sieved to provide an average particle size of 20–75 µm by jet sieve.

Aqueous pharmaceutical composition: Diphtheria toxoids vaccine (DPT) (2%), mannitol (30%), glycine (8%), and trehalose (60%) at a total solid concentration of 10%.

Spray coater: Precision coater (MP-1, Niro), operated at the following coating conditions: air inlet temperature=75° C., air outlet temperature=40° C., liquid feed=13 mL/min, air velocity in the bed=3.5 m/sec., coating loading 0.5% of DPT, and a coating time=58 min.

The spray-coated powder formulation of each Example is suitable for transdermal administration from a needleless syringe and is characterized in that the individual spray-coated particles have an average size in the range of about 20 to 70 µm, an envelope density ranging from about 0.1 to about 25 g/cm$^3$, preferably ranging from about 0.8 to about 1.5 g/cm$^3$, and have a substantially spherical aerodynamic shape with a substantially uniform, nonporous surface.

Accordingly, novel spray-coated powder compositions, and methods for producing these compositions have been described. Although preferred embodiments of the subject invention have been described in some detail, it is understood that obvious variations can be made without departing from the spirit and the scope of the invention as defined by the appended claims.

What is claimed is:

1. A method for preparing a spray-coated powder for administration from a needleless syringe, said method comprising spray-coating an aqueous pharmaceutical composition onto seed particles under conditions sufficient to provide coated particles having an axis ratio of 3 or less, an average size of about 10 to 100 µm and an envelope density ranging from about 0.1 to about 25 g/cm$^3$.

2. The method of claim 1 comprising the steps of:
   (a) suspending the seed particles in a reaction chamber using a heated air flow;
   (b) atomizing an aqueous pharmaceutical composition into a spray and introducing said spray into the reaction chamber;
   (c) allowing the spray to spread over the surface of said suspended seed particles to coat said seed particles with a film; and
   (d) drying the coated seed particles.

3. The method of claim 2, wherein the aqueous pharmaceutical composition is sprayed into the reaction chamber in a direction that is transverse to the direction of the hot air flow.

4. The method of claim 1, wherein the pharmaceutical composition comprises a peptide, protein or a fragment thereof.

5. The method of claim 1, wherein the pharmaceutical composition comprises a vaccine.

6. The method of claim 5, wherein the vaccine is a peptide vaccine.

7. The method of claim 6, wherein the peptide vaccine component comprises a synthetic peptide.

8. The method of claim 1, wherein said seed particles are crystalline particles.

9. The method of claim 1, wherein the seed particles have an axis ratio of 2 or less.

10. The method of claim 1, wherein the seed particles are selected from the group consisting of lactose, mannitol, trehalose, polysaccharides, starches, and biodegradable polymers.

11. The method of claim 1, wherein said coated seed particles have an average size of about 20 to 70 µm.

12. The method of claim 1, wherein said coated seed particles have an envelope density ranging from about 0.8 to about 1.5 g/cm$^3$.

13. The method of claim 1, wherein said coated seed particles have a substantially spherical aerodynamic shape.

14. The method of claim 1, wherein said coated seed particles have a substantially uniform, nonporous surface.

15. The method of claim 1, wherein said coated seed particles have pharmaceutical composition loading of about 1 to 50 wt %.

16. A dosage receptacle for needleless syringe comprising a therapeutically effective amount of a spray-coated powder composition comprising seed particles coated with a pharmaceutical composition, wherein said coated seed particles have an axis ratio of 3 or less, an average size of about 10 to 100 µm, and an envelope density ranging from about 0.1 to about 25 g/cm$^3$.

17. The dosage receptacle of claim 16, wherein said receptacle is selected from the group consisting of capsules, foil pouches, sachets and cassettes.

18. The dosage receptacle of claim 16, wherein said coated seed particles are crystalline particles.

19. The dosage receptacle of claim 16, wherein said coated seed particles have an axis ratio of 2 or less.

20. The dosage receptacle of claim 16, wherein said coated seed particles are selected from the group consisting of lactose, mannitol, trehalose, polysaccharides, starches, and biodegradable polymers.

21. The dosage receptacle of claim 16, wherein said coated seed particles have an average size of about 20 to 70 µm.

22. The dosage receptacle of claim 16, wherein said coated seed particles have an envelope density ranging from about 0.8 to about 1.5 g/cm$^3$.

23. The dosage receptacle of claim 16, wherein said coated seed particles have a substantially spherical aerodynamic shape.

24. The dosage receptacle of claim 16, wherein said coated seed particles having a substantially uniform, nonporous surface.

25. The dosage receptacle of claim 16, wherein said coated seed particles having a pharmaceutical composition loading of about 1 to 50 wt %.

26. A needleless syringe comprising a therapeutically effective amount of a spray-coated powder composition comprising seed particles coated with a pharmaceutical composition, wherein said coated seed particles have an axis ratio of 3 or less, an average size of about 10 to 100 µm, and an envelope density ranging from about 0.1 to about 25 g/cm$^3$.

27. The needleless syringe of claim 26, wherein said coated seed particles are crystalline particles.

28. The needleless syringe of claim 26, wherein said coated seed particles have an axis ratio of 2 or less.

29. The needleless syringe of claim 26, wherein said coated seed particles are selected from the group consisting of lactose, mannitol, trehalose, polysaccharides, starches, and biodegradable polymers.

30. The needleless syringe of claim 26, wherein said coated seed particles have an average size of about 20 to 70 µm.

31. The needleless syringe of claim 26, wherein said coated seed particles have an envelope density ranging from about 0.8 to about 1.5 g/cm$^3$.

32. The needleless syringe of claim 26, wherein said coated seed particles have a substantially spherical aerodynamic shape.

33. The needleless syringe of claim 26, wherein said coated seed particles have a substantially uniform, nonporous surface.

34. The needleless syringe of claim 26, wherein said coated seed particles have a pharmaceutical composition loading of about 1 to 50 wt %.

* * * * *